(12) United States Patent
Bishop et al.

(10) Patent No.: US 8,308,809 B2
(45) Date of Patent: Nov. 13, 2012

(54) METHOD OF IMPLANTING AN IMPLANT INCLUDING BONE ABRASION

(75) Inventors: Nick Bishop, Hamburg (DE); Gary Moore, Leeds (GB); Michael Morlock, Hamburg (DE)

(73) Assignee: Depuy International Limited (GB)

( * ) Notice: Subject to any disclaimer, the term of this patent is extended or adjusted under 35 U.S.C. 154(b) by 152 days.

(21) Appl. No.: 12/746,609

(22) PCT Filed: Dec. 1, 2008

(86) PCT No.: PCT/GB2008/051138
§ 371 (c)(1),
(2), (4) Date: Aug. 2, 2010

(87) PCT Pub. No.: WO2009/071940
PCT Pub. Date: Jun. 11, 2009

(65) Prior Publication Data
US 2010/0298944 A1  Nov. 25, 2010

(30) Foreign Application Priority Data

Dec. 8, 2007  (GB) .................... 0724019.5

(51) Int. Cl.
*A61F 2/30* (2006.01)
*A61F 2/46* (2006.01)

(52) U.S. Cl. ............. 623/22.12; 623/23.11; 623/23.42
(58) Field of Classification Search ........... 623/22.12, 623/22.15, 22.4, 22.42, 22.43, 22.45, 23.11, 623/23.12, 23.42, 23.43, 23.46
See application file for complete search history.

(56) References Cited

U.S. PATENT DOCUMENTS

| | | | |
|---|---|---|---|
| 3,855,638 A | 12/1974 | Pilliar | |
| 4,328,593 A * | 5/1982 | Sutter et al. | 623/23.42 |
| 4,714,470 A | 12/1987 | Webb, Jr. et al. | |
| 5,507,830 A * | 4/1996 | DeMane et al. | 623/22.42 |
| 2003/0065401 A1 | 4/2003 | Amrich | |
| 2004/0024468 A1* | 2/2004 | Lualdi et al. | 623/22.45 |
| 2004/0193276 A1* | 9/2004 | Maroney et al. | 623/19.14 |
| 2004/0193278 A1* | 9/2004 | Maroney et al. | 623/19.14 |
| 2005/0245934 A1 | 11/2005 | Tuke | |
| 2006/0015111 A1* | 1/2006 | Fenton | 606/80 |

FOREIGN PATENT DOCUMENTS

| | | |
|---|---|---|
| EP | 1356795 A1 | 10/2003 |
| EP | 1388329 A1 | 2/2004 |
| EP | 1470802 A1 | 10/2004 |
| EP | 1549230 B1 | 1/2007 |
| GB | 764600 A | 12/1956 |
| WO | WO 2004032767 A1 | 4/2004 |

OTHER PUBLICATIONS

UK Search Report GB0724019.5 dated Apr. 4, 2008.
PCT International Written Opinion and Search Report PCT/GB2008/051138 dated Mar. 26, 2009.

* cited by examiner

*Primary Examiner* — David Isabella
*Assistant Examiner* — Randy Shay

(57) ABSTRACT

An implant assembly having an articulating surface and an axial cavity arranged to receive an end of a bone, the axial cavity being generally circular in cross section in a plane normal to the axis of the implant, and including a spacing element detachable from the implant. At least a portion of the interior surface of the cavity is roughened and is arranged to abrade bone when the end of the bone is received in the cavity. The spacing element is arranged to prevent the implant from fully seating on the end of the bone such that the implant and the end of the bone are in a predetermined spaced apart arrangement.

2 Claims, 1 Drawing Sheet

METHOD OF IMPLANTING AN IMPLANT INCLUDING BONE ABRASION

CROSS REFERENCE TO RELATED PCT APPLICATION

This application is filed pursuant to 35 U.S.C. 371 as a National Stage application of International Patent Application PCT/GB2008/051138, filed Dec. 2, 2008.

BACKGROUND OF THE INVENTION

The present invention relates to an implant assembly. In particular, but not exclusively, the present invention relates to an implant assembly for implanting a resurfacing implant to replace an articulating surface at the end of a bone which forms the ball component of a ball and socket joint. Certain embodiments of the present invention comprise an implant that is provided with a roughened bone engaging surface to prepare the bone surface so as to accurately shape the end of the bone to fit a cavity within the implant. Embodiments of the implant assembly further includes a spacer sleeve releasably coupled to the implant during the bone preparation in order to position the implant correctly relative to the bone.

BRIEF SUMMARY OF THE INVENTION

Conventional orthopaedic joint prostheses for replacing ball and socket joints comprise an implanted socket prosthesis component and an implanted ball prosthesis component. Implantation of the ball prosthesis component typically involves removal of a large portion of the ball end of the bone, including all of the ball component and much or all of any neck at the end of the bone, in a process known as resection. The ball prosthesis component comprises a stem which is inserted into the open medullary canal of the resected bone. The stem terminates at a proximal end at a neck portion coupled to a head component formed as a partial sphere. The head component comprises a bearing surface which articulates within the implanted socket component.

It is known to replace only the articulating surface at the end of a bone in preference to removing and replacing a significant portion of the bone. In such a "resurfacing" joint prosthesis, the bone tissue that provides the ball component of a ball and socket joint (for example the humeral component of a shoulder joint or the femoral component of a hip joint) is prepared to receive a cap-like component having an outer bearing surface which can be received in the socket component of the joint prosthesis. Preparation of the bone involves shaping the bone tissue of the ball component of the natural joint so that its external shape is approximately the same as the shape of a cavity within the cap-like component. The cavity is rotationally symmetrical. Preparation further involves drilling a bore in the end of the bone in which a central locating implant pin of the cap-like component can be located. The resurfacing implant can then be implanted over the prepared bone end and secured in position using an impaction force, to create a press fit, or using bone cement.

It is known to use a reamer tool to prepare a bone for implantation of a component of an orthopaedic joint prosthesis. A reamer includes cutting teeth which can be moved against the bone surface to cut the bone. The reamer can be moved reciprocally along an axis to cut the bone, when the cutting teeth are arranged so that they face along that axis. In such a case the cutting teeth may be provided on the end of a wall of a reamer body similar to the teeth provided on a saw. A reamer may also have cutting teeth defined by slits in the wall of a reamer body. The material of the reamer body is deformed out of the plane of the reamer wall at each slit to provide a cutting tooth (alternatively referred to as "slit-like cutting teeth").

In order to prepare the end of a bone to receive a resurfacing component of a joint prosthesis, it is known to use a reamer assembly to remove the articulating surface of the bone so that the bone can receive the cap-like component. The reamer may comprise a reamer guide and a reamer shell with a sleeve portion which is a sliding fit upon the reamer guide.

Such a reamer assembly for preparing the ball component of a natural ball and socket joint for a resurfacing joint prosthesis is described in EP-1549230B1 ("A Reamer Assembly", DePuy International Limited). The reamer assembly is described as being particularly suitable for preparing the ball component of a hip joint for resurfacing. The reamer guide comprises an elongate member which can be implanted within a bore cut into the end surface of the natural ball component of the joint along an axis defined by the sphere of the bearing surface. The reamer shell is arranged to cut bone around the reamer guide to a desired shape. The reamer guide comprises a sleeve portion at a proximal end which is arranged to slide over the reamer guide and a shell wall which extends distally from the sleeve in a generally cylindrical or conical fashion to a cutting edge at the distal end of the shell which engages and cuts the bone as the shell is rotated about the reamer guide. Slit like cutting teeth may also be provided in the shell wall to remove portions of the ball component of the bone, in particular those portions of the bone at the existing bearing surface of the joint.

The resurfacing implant is then implanted over the prepared bone. The implant comprises an external convex bearing surface and an internal cavity. The cavity is generally cylindrical or conical and is sized to receive the prepared bone end. A central locating implant pin within the cavity is received within the bore in the end of the bone and assists in accurately aligning the implant. The resurfacing implant is then driven home over the bone end by an impaction force.

It is known to secure orthopaedic joint prostheses using an adhesive (also referred to as bone cement). Alternatively, it is known to secure joint prostheses using techniques that do not use cement. For instance, it is known that if the surface of the bone can be brought into close proximity to the implant then bone growth around and over the prosthesis can secure the prosthesis in position. Furthermore it is known that if at least the surface of the prosthesis comprises a porous structure then bone growth can be encouraged through the cavities of the porous structure firmly embedding the prosthesis within the bone. As the bone is embedded into the prosthesis, the interface between the bone and the prosthesis and the bone is merged increasing the joint strength.

Such a porous structure can be provided as a porous coating applied to the prosthesis. Alternatively, part or all of the prosthesis can be formed from a material that is itself a porous structure.

Various porous coatings have been found to be effective, for example a porous coating is described in U.S. Pat. No. 3,855,638. One particularly effective coating is applied to prosthesis components available from DePuy Orthopaedics Inc under the trademark Porocoat. Porocoat is a porous coating that comprises a beaded coating that may, for instance, be sintered onto the underlying material of the prosthesis. The porous coating consists of a plurality of small discrete particles of a metallic material bonded together at their points of contact with each other to define a plurality of connected interstitial pores in the coating. Typically, the particles are formed of the same metallic material as the material from which the substrate is formed. Bone regrowth through the interstitial pores fixes the implant in position.

A porous coating can be applied to inside of the cavity of a resurfacing implant in order to secure the resurfacing implant into position.

In order to securely fix a resurfacing implant to the end of the bone it is important to ensure that the end of the bone is accurately prepared such that it is a close fit for the cavity of the resurfacing implant. How securely the implant is seated is greatly affected by the degree of interference between the prepared bone and the cavity. For implants that are to be fixed into position without cement, using a porous structure, the amount of interference between the prepared bone end and the porous structure significantly affects the resulting strength of the implant. If the prepared bone is poorly sized for the implant cavity it may even be difficult to fully seat the implant to its final position at all.

Inaccurate preparation of the bone end can result in a range of problems. In addition to having difficulty in fully seating the implant, excess exposed cut bone may be left uncovered by the implant. It is desirable that as little bone is cut away as possible during implantation of a resurfacing prosthesis to preserve the integrity of the remaining bone and thereby increase its strength. Difficulty in seating the implant can result in excessive impaction forces being applied, risking further damage to the bone. This can occur if there is too much contact between the bone and the implant, that is if the fit is too tight. A poorly positioned implant may not transfer loads correctly to the bone, risking further damage to the bone later on. Conversely, if the implant fit is loose, its position may vary over time risking further damage when the joint is loaded. Furthermore, if the fit is too loose then bone in-growth into the porous structure is inhibited, resulting in a weaker joint.

It is an object of the present invention to obviate or mitigate one or more of the problems associated with the prior art, whether identified herein or elsewhere. In particular, it is an object of embodiments of the present invention to provide an implant assembly that ensures that a prepared end of a bone is correctly sized for a resurfacing implant such that the resurfacing implant is a close fit.

According to a first aspect of the present invention there is provided an implant assembly comprising: an implant forming one component of a joint prosthesis, the implant comprising an articulating surface and an axial cavity arranged to receive an end of a bone, the axial cavity being generally circular in cross section in a plane normal to the axis of the implant; and a spacing element detachable from the implant; wherein at least a portion of the interior surface of the cavity is roughened and is arranged to abrade bone when the end of the bone is received in the cavity, the spacing element being arranged to prevent the implant from fully seating on the end of the bone such that the implant and the end of the bone are in a predetermined spaced apart arrangement An advantage of the first aspect of the present invention is that because the implant assembly includes the implant itself, when the implant assembly is used to prepare an end of a bone this ensures that the end of the bone will accurately match the implant cavity once the spacing element has been removed and the implant is fully seated on the bone using an impaction force. The implant assembly, with the spacing element attached to the implant is used to prepare the bone surface at the end of the bone by rotating the implant while axial pressure brings the roughened surface to bear against the bone. The spacing element prevents too much bone from being abraded such that with the spacing element removed the implant will form a tight compression fit. The spacing element prevents the implant from being fully seated upon the end of the bone by preserving the cavity at least partially open. This prevents excess bone from being abraded by limiting the extent to which the implant can travel along the axis of the bone.

Preferably, the implant further comprises an implant pin projecting axially from the closed end of the cavity.

Advantageously, the spacing element comprises a spacer sleeve having an axial bore arranged to releasably receive the implant pin and an outer surface arranged to be inserted into a bore provided in the end of the bone. The spacer sleeve serves to ensure that the implant remains correctly aligned with the bone. The exterior surface of the spacer sleeve forms a sliding fit within the cylindrical bore within the end of the bone.

The spacer sleeve may further comprise an annular collar arranged to space the closed end of the cavity away from the end of the bone. The collar may be less than 5 mm thick in a direction parallel to the axis of the implant. Advantageously, the spacer sleeve collar spaces the implant away from the head of the bone by being impinged between the two.

Preferably, the interior surface of the cavity diverges from the axis of the implant towards its open end. More preferably, the angle between the interior surface of the cavity and the axis of the implant is less than 5°.

Preferably, the axial bore of the spacer sleeve tapers towards its closed end and the implant pin tapers towards its free end, the exterior surface of the spacer sleeve generally forming a cylinder.

The spacer sleeve may be formed from a plastics material and the implant may be formed substantially from a metallic material Preferably, the roughened surface comprises a porous structure adapted to encourage bone ingrowth. The porous structure may comprise a porous coating applied to at least a portion of the interior surface of the cavity.

The implant may comprise a femoral resurfacing implant and the joint prosthesis comprises a hip joint prosthesis.

According to a second aspect of the present invention there is provided a method of implanting an implant forming one component of a joint prosthesis, the implant comprising an articulating surface and an axial cavity, the axial cavity being generally circular in cross section in a plane normal to the axis of the implant, at least a portion of the interior surface of the cavity being roughened, the implant being detachably coupled to a spacing element, the method comprising: receiving the end of a bone in the cavity, the spacer sleeve preventing the implant from fully seating on the end of the bone such that the implant and the end of the bone are in a predetermined spaced apart arrangement; rotating the implant assembly while applying axial pressure to the implant in the direction of the bone such that bone is abraded by the roughened surface; removing the implant from the end of the bone; removing the spacing element from the implant; positioning the implant over the end of the bone such that the end of the bone is inserted into the cavity; and applying an axial impaction force to the implant until the implant is fully seated upon the end of the bone.

The method may further comprise drilling the bore into the end of the bone and forming the end of the bone to the approximate shape of the cavity prior to positioning the implant assembly over the end of the bone.

BRIEF DESCRIPTION OF THE DRAWINGS

Embodiments of the present invention will now be described, by way of example only, with reference to the accompanying drawings in which.

DETAILED DESCRIPTION OF THE INVENTION

Figure 1:
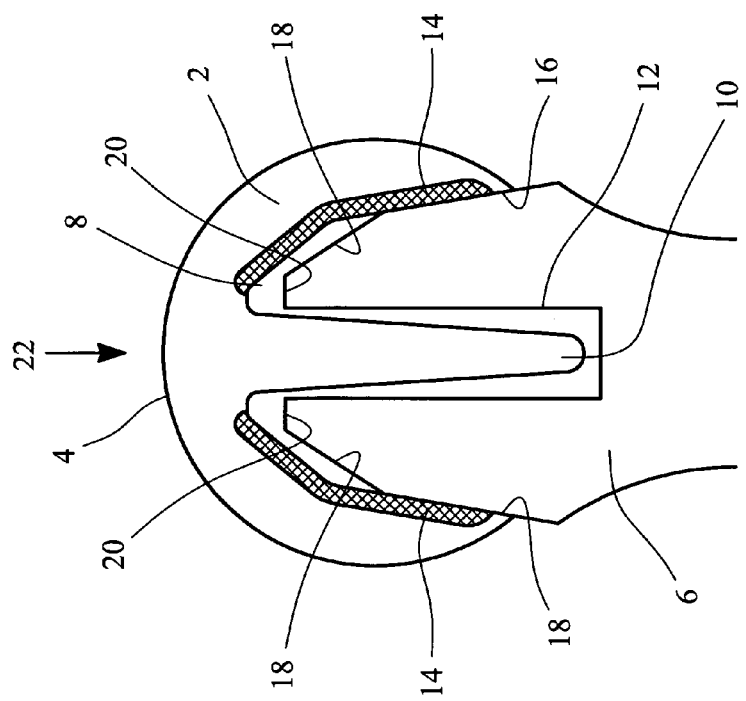
FIG. 1 schematically illustrates in cross section a conventional resurfacing joint prosthesis during implantation over a prepared end of a bone forming the ball component of a ball and socket joint.

Referring to FIG. 1, this schematically illustrates a conventional resurfacing implant 2 which forms part of a orthopaedic joint prosthesis. In particular, resurfacing implant 2 forms the femoral component of a hip joint prosthesis and provides a partially spherical articulating surface 4 that is received within an implanted acetabulum prosthesis (not shown). The resurfacing joint prosthesis 2 provides a hard wearing bearing surface 4 on the head of a femur 6

FIG. 1 is illustrated in cross section, and further illustrates the prepared end of the femur 6. The prepared femur 6 is received within an axial cavity 8 formed within the resurfacing implant 2. The axial cavity 8 is generally cylindrical or conical about the axis of the implant 2. FIG. 1 illustrates the implant 2 not yet fully seated upon prepared femur 6, such that the cavity 8 is still partially open.

The resurfacing implant 2 further comprises an axial implant pin 10 which is received within an axial bore 12 within the prepared end of the femur 6. The bore may be cylindrical or may taper toward its closed end. The implant pin 10 serves to ensure that the resurfacing implant 2 is correctly aligned with the prepared end of the femur 6 before the implant 2 is implanted.

At least part of the interior surface of the cavity 8 is provided with a porous structure 14 such as a layer of Porocoat® coating. The porous structure 14 serves to secure the implant 2 into position as natural bone can grow through the pores to firmly bond the implant into position.

Conventionally, the preparation of the head of the femur 6 to receive the resurfacing implant 2 involves first forming a bore 12 along or at a desired angle to the axis of the femoral head to receive the implant pin 10. The external surface of the femur 6 is prepared by the formation of three rotationally symmetrical reamed surfaces 16, 18 and 20. A first surface 16 is generally aligned parallel or close to parallel to the axis of the bore 12. The second surface extends between the first surface and a third surface at about 135°. The third surface is generally formed as a plane normal to the axis of the bore 12. The surfaces 16-20 may be formed using a reamer as described above in the introduction.

Once the femoral head is prepared, the resurfacing implant 2 is positioned over the femoral head such that the implant pin 10 is aligned with the bore 12 and the implant 2 is driven onto the femur 6 using an impaction force provided along the axis of the implant pin, in the direction indicated by arrow 22. The resurfacing implant 2 is driven along the axis of the implant pin 10 until the implant 2 is fully seated upon the femur 6 (FIG. 1 illustrates an intermediate position in which the implant 2 has not yet been fully seated such that the axial cavity 8 is still partially open between the upper surface 20 of the femur 6 and the closed end of cavity 8).

However, as discussed above in the introduction, if the end of the femur 6 is not accurately matched to the axial cavity 8 of the implant 2 then problems can occur. If the end of the femur is too small then the implant may be loose, or become loose during normal use. This may be due to the presence of a gap between the femur and part or all of the porous structure 14, which inhibits bone in growth. Alternatively, if the femur is too large then it can be difficult to fully seat the implant 2 into its final position, such that either axial cavity 8 remains partially open, or excessive damaging force is required. Incorrect seating of the implant 2 can result in the implant not correctly transferring loads to the bone, resulting in increased wear of the implant and possible damage to the bone, which can result in the implant loosening.

Problems in sizing the prepared end of femur 6 are due in part to tolerance stack up between the reamer used to prepare the bone and the implant 2. This can result in there being too much or too little surface area contact between the bone and the implant. Furthermore, using a separate reamer to prepare the bone does not allow the fit between the implant and the bone to adjusted prior to the implant being attached using the axial impaction force. As the exact dimensions of implants can vary, using a separate reamer to prepare the bone does not allow for adjustment of the bone specific to a particular implant.

Figure 2:
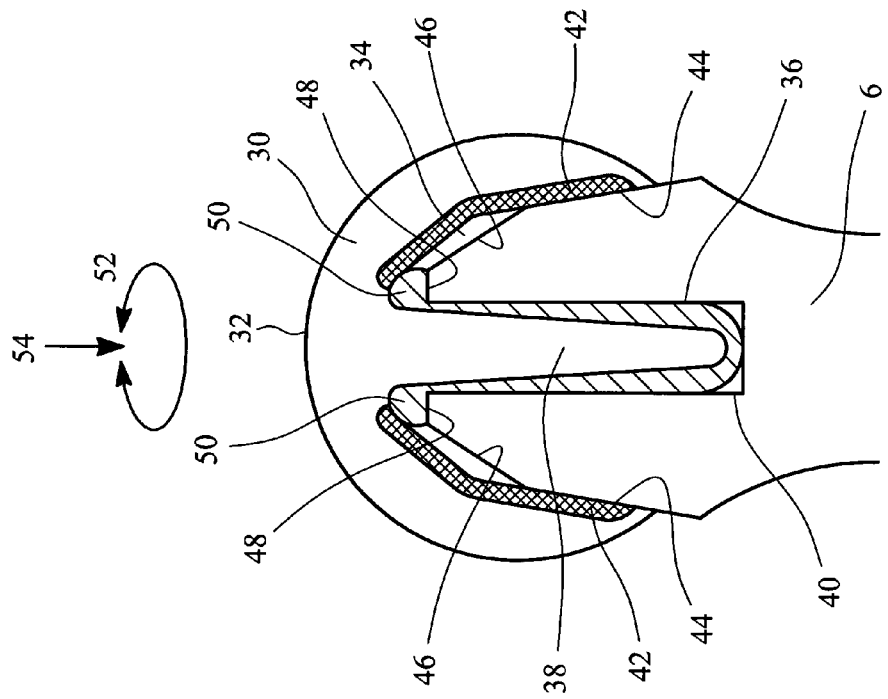
FIG. 2 schematically illustrates an implant assembly comprising a resurfacing implant and a spacer sleeve in accordance with an embodiment of the present invention being used to prepare a ball component of a natural ball and socket joint before final implantation of the resurfacing implant.

FIG. 2 illustrates in cross section an implant assembly in accordance with an embodiment of the present invention. The implant assembly comprises a resurfacing implant 30 which forms part of an orthopaedic joint prosthesis. In particular, resurfacing implant 30 forms the femoral component of a hip joint prosthesis and provides a partially spherical articulating surface 32 that it received within an implanted acetabulum prosthesis (not shown). The resurfacing joint prosthesis 30 provides a hard wearing bearing surface 32 on the head of a femur 6.

FIG. 2 further illustrates the prepared end of the femur 6. In accordance with embodiments of the present invention the femur 6 may be initially prepared using a reamer as described above in order to approximately size the femur 6 to be received within an axial cavity 34 within the implant 30. FIG. 2 illustrates the implant assembly during an intermediate stage during which the implant assembly is used to accurately prepare the approximately prepared femur 6. Because the implant assembly includes the resurfacing implant 30, the finally prepared femur 6 matches the axial cavity 34 more accurately than if the femur 6 was prepared only using a separate reamer.

The axial cavity 34 is generally cylindrical or conical about an axis of the implant 30 defined by the partial sphere of the articulating surface 32. The implant assembly further comprises a spacer sleeve 36. The spacer sleeve 36 is located about implant pin 38 which extends axially from the closed end of axial cavity 34. When the implant assembly is being used to finalise the preparation of the femur 6, the spacer sleeve 36 and the implant pin 38 are received within an axial bore 40 within the end of the femur 6. The implant pin 38 and the spacer sleeve 36 serve to ensure that the resurfacing implant 30 is correctly aligned with the prepared end of the femur 6 during final preparation of the exterior surfaces of the femur 6. Once the femur 6 has been fully prepared, the spacer sleeve 36 is removed before the implant 30 is fully seated upon the end of the femur.

At least part of the interior surface of the cavity 34 is provided with a porous structure 42 such as a layer of Porocoat® coating. The porous structure 42 serves to secure the implant 30 into position once the implant 30 is finally seated upon femur 6 as natural bone can grow through the pores to firmly bond the implant into position. Furthermore, during final preparation of the femur 6 using the implant assembly, the porous structure serves to abrade surface portions of the bone in order to ensure a close fit between the implant 30 and the femur 6.

The preparation of the head of the femur 6 to receive the resurfacing implant 30 involves first forming bore 40 along or at a desired angle to the axis of the femoral head to receive the implant pin 38 and the spacer sleeve 36. The external surface of the femur 6 is then approximately prepared by the formation of three rotationally symmetrical reamed surfaces 44, 46 and 48 A first surface 44 is generally aligned close to parallel to the axis of the bore 40, though at an angle of approximately 3° to the axis of the bore 40, as will be described in greater detail below. The second surface 46 extends between the first surface and a third surface at an angle of about 135°. The third surface 48 is generally formed as a plane normal to the axis of the bore 40 The surfaces 44, 46, 48 may be formed using a reamer as described above.

The embodiment of the present invention illustrated in FIG. 2 comprises an implant assembly which comprises a resurfacing implant 30 and a spacer sleeve 36 that allows for a repeatable method of reducing the amount of interference between the prepared bone 6 and the inner surface of the axial cavity 34. Spacer sleeve 36 comprises a one piece sleeve having an interior bore that closely matches the tapering implant pin 38. The exterior surface of the spacer sleeve 36 comprises a cylinder having generally parallel sides that is arranged to form a close sliding fit within the bore 40 in the end of femur 6. That is, the spacer sleeve is thicker at its distal end than at its end proximal the closed end of cavity 34. The spacer sleeve 36 further comprises a flanged portion 50 that forms an axial collar about the end of implant pin 38 at the closed end of cavity 34. Flange 50 rests upon bone surface 48 and prevents the implant 30 from fully seating upon femur 6 during preparation of the femur 6.

As described above, the femur 6 is first approximately shaped using, for instance, a reamer as described above in the introduction. The end of the femur 6 is arranged to be slightly larger in circumference that the axial cavity 34. In order to finally prepare the femur 6 to exactly fit the axial cavity 34, the spacer sleeve 36 is placed over the implant pin 38 and the spacer sleeve is inserted into bore 40 in the end of femur 6. The implant 30 is pushed along the axis of bore 40 until the interior surfaces of axial cavity 34 contact the exterior surfaces of the femur 6. The implant assembly is then rotated in either direction as indicated by arrow 52 while axial pressure is applied forcing the implant assembly onto femur 6. Due to the porous structure 42 such as a layer of Porocoat® coating, the interior surfaces of cavity 34 are abrasive. As the implant assembly is rotated a small amount of bone is removed from at least portions of surfaces 44 and 46 providing an accurately controlled final preparation to bone 6 that is unique to the particular implant 30.

The rotation and axial pressure is continued until the flange 50 prevents further axial motion of the implant assembly by being trapped between bone surface 48 and the closed end of the cavity 34.

Once the femoral head is thus finally prepared, the spacer sleeve 36 is removed and the resurfacing implant 30 is positioned over the femoral head such that the implant pin 38 is aligned with the bore 40 and the implant 30 is driven on to the femur 6 using an impaction force provided along the axis of the implant pin 38 in the direction indicated by arrow 54. The resurfacing implant 30 is driven along the axis of the implant pin 38 until the implant 30 is fully seated upon the femur 6.

As the prepared bone and the axial cavity taper, that is narrow in cross section, towards the closed end of the cavity or the free end of the bone, forcing the implant 30 onto the femur 6 forms an interference fit that firmly locks the implant in position. As the femur 6 is finally prepared using the implant 30 itself, an accurate fit is ensured, such that the fit is close, without requiring an excessive impaction force. The prepared bone 6 slightly compresses as the implant 30 is driven onto it. This compression serves to secure the bone in position. Furthermore, accurately sizing the femur 6 using the implant 30 ensures that the bone is compressed correctly, that is not too much which could result in difficulty in fully seating the implant 30, and not too little, which could result in a loose fit for the implant 30.

In order to ensure a close interference fit between the femur 6 and the axial cavity 34 it is preferable that the taper of the axial cavity wall and the prepared femur relative to the axis of the implant pin 38 is less than 10°. More preferably, the taper is less than 5°, for instance about 3°.

The height of flange 50 along the axis of bore 40 also determines the degree of compression of the bone as the implant 30 is finally driven onto the prepared tapering bone. The height of the flange is preferably less than 10 mm. More preferably, the height is less than 5 mm. Most preferably the height of flange 50 is between about 2 mm and about 3 mm.

The degree of compression of the bone when the implant 30 is fully seated upon femur 6 is a key factor in determining how firmly the implant is attached. The smaller the angle of the walls of the cavity and the prepared femur to the axis of the implant pin, the tighter the interference fit will be. Additionally, a tighter fit and more compression is achieved for a taller flange 50.

Spacer sleeve 36 may suitably be formed from a plastics material, for instance polyethylene. However, any suitable bio-compatible material may be used that can be releasably mounted upon implant pin 38.

In alternative embodiments of the present invention, the spacer sleeve may be truncated. That is, the spacer sleeve may not extend all of the way to the free end of the implant pin, and therefore be open ended. Separation between the end of the bone and the closed end of the implant cavity is still caused by the flange.

The spacer sleeve may be formed from two separate components: a sleeve component and spacing component (that is, a separate flange).

Embodiments of the present invention consistently refer to a spacer sleeve. However, it will be readily apparent to the appropriately skilled person that the primary purpose of the spacer sleeve is to space the implant apart from the end of the bone such that it cannot be fully seated on the end of the bone. This controls the amount of bone that is removed from the peripheral external surface of the end of the bone and thereby accurately controls the shape of the end of the bone and ensures an accurately controlled fit. Thus, the spacer sleeve may be replaced in alternative embodiments of the present invention by other spacing elements that achieve this effect. For instance, if the implant includes an implant pin, then a spacing element may be formed as a simple annular ring or collar about the implant that is seated upon the end surface of the bone. Alternatively, the spacing element could form a cap that fits only over the tip of the implant pin and thus prevents the implant pin from being fully inserted into the bore within the end of the bone (note, that such a spacing element requires that the depth of the bore is closely controlled). Further spacing elements may be formed not as initially separate components, but rather as a part of the implant that may be detached once the end of the bone is fully prepared. For instance, such a detachable spacing element could form one or more protrusion in the closed end of the cavity coupled to the remainder of the implant via a narrow section of material that may be snapped off. Further alternative forms of spacing element will be readily apparent to the appropriately skilled person from the teaching herein, without departing from the scope of the appended claims.

In alternative embodiments, the implant pin need not taper: it could be cylindrical. In such an embodiment the spacer sleeve may be of constant thickness along its length. For an implant pin having parallel sides the spacing element may comprises a ring or a washer. The parallel sides of the implant pin reduce the risk of the ring falling off during preparation of the end of the bone, if the ring is a tight fit about the implant pin.

Advantageously, accurately sizing the prepared femur 6 using the resurfacing implant 30 itself as part of an implant assembly provides for a closely controlled fit between the bone and the implant obviating the problems identified above relating to a poor size match between the femur and the implant. In particular, as the implant 30 is fully seated, bone ingrowth into the porous structure is encouraged resulting in a stronger implant. As the implant is fully seated, the possibility of cut bone being left exposed is reduced. Bone ingrowth into the porous structure may be encouraged as during rotation of the implant assembly the porous structure may be impregnated with bone material.

While the present invention has been predominantly described herein in the context of the implantation of a resurfacing implant onto the head of a femur, it will be readily apparent the invention is not limited to this. The present invention may be readily applied to any situation in which as prosthesis is to be applied to the end of a bone, for instance a resurfacing humeral component of a prosthetic shoulder joint. Further advantages and applications of the present invention will be readily apparent to the appropriately skilled person without departing from the scope of the appended claims.

The invention claimed is:

1. A method of implanting an implant forming one component of a joint prosthesis, the implant comprising an articulating surface and an axial cavity, the axial cavity being generally circular in cross section in a plane normal to the axis of the implant, at least a portion of the interior surface of the cavity comprising a roughened surface, the implant being detachably coupled to a spacing element, the method comprising the steps of:

disposing at least the end of a bone in the cavity, the spacer element preventing the implant from fully seating on the end of the bone such that the implant and the end of the bone are in a predetermined spaced apart arrangement;

rotating the implant while applying axial pressure to the implant in the direction of the bone such that bone is abraded by the roughened surface;

removing the implant from the end of the bone;

removing the spacing element from the implant;

positioning the implant over the end of the bone such that the end of the bone is at least partially disposed within the cavity; and applying an axial impaction force to the implant until the implant is seated upon the end of the bone.

2. The method of claim 1, further comprising the steps of drilling a bore into the end of the bone and forming the end of the bone to the approximate shape of the cavity prior to positioning the implant over the end of the bone.

* * * * *